United States Patent
DeFeo

(10) Patent No.: US 10,307,282 B1
(45) Date of Patent: Jun. 4, 2019

(54) APPARATUS AND METHODS FOR TREATMENT OF PLANTAR FASCIITIS

(71) Applicant: Michael DeFeo, Garden City, NY (US)

(72) Inventor: Michael DeFeo, Garden City, NY (US)

( * ) Notice: Subject to any disclaimer, the term of this patent is extended or adjusted under 35 U.S.C. 154(b) by 627 days.

(21) Appl. No.: 14/974,116

(22) Filed: Dec. 18, 2015

Related U.S. Application Data

(60) Provisional application No. 62/094,545, filed on Dec. 19, 2014.

(51) Int. Cl.
*A61F 5/01* (2006.01)

(52) U.S. Cl.
CPC .................. *A61F 5/0111* (2013.01)

(58) Field of Classification Search
CPC .... A61F 5/0111; A61F 5/0113; A61F 5/0127; A61F 5/0195; A61F 5/0585; A61F 5/0123
See application file for complete search history.

(56) References Cited

U.S. PATENT DOCUMENTS

| | | | |
|---|---|---|---|
| 4,693,470 A | 9/1987 | Ogawa | |
| 4,930,767 A * | 6/1990 | Hamm | A63B 21/0552 482/124 |
| 5,399,155 A | 3/1995 | Strassburg et al. | |
| 6,110,078 A | 8/2000 | Dyer | |
| 6,379,321 B2 | 4/2002 | Gaylord et al. | |
| 7,179,206 B2 | 2/2007 | Backes et al. | |
| 7,753,864 B2 | 7/2010 | Beckwith et al. | |
| 7,806,844 B2 | 10/2010 | Outred et al. | |
| 8,216,162 B2 | 7/2012 | Bushby | |
| 8,241,232 B2 * | 8/2012 | Sanders | A61H 1/0266 36/11.5 |
| 8,409,123 B2 * | 4/2013 | Hoffmeier | A61F 5/0113 128/846 |
| 8,475,397 B2 | 7/2013 | Chiu et al. | |
| 2009/0264803 A1 * | 10/2009 | Darby, II | A61F 5/0111 602/27 |

(Continued)

OTHER PUBLICATIONS

Theraband, "Foot Roller Product Description," http://www.theraband.com/store/products.php?ProductID=58, 2014,1 page.

(Continued)

*Primary Examiner* — Ophelia A Hawthorne
(74) *Attorney, Agent, or Firm* — Ryan, Mason & Lewis, LLP

(57) ABSTRACT

An apparatus for treatment of plantar fasciitis comprises a first anchor adapted for securing around a leg of a patient, a second anchor adapted for securing around a foot of the leg, first and second toe straps each adapted for attachment between the first and second anchors so as to provide respective first and second dorsiflexion forces to respective first and second subsets of toes of the foot, and a fascia compression strap comprising first and second ends and an intermediate portion between the first and second ends, the first and second ends each adapted for attachment to the first anchor so as to provide static pressure to an underside of the foot via the intermediate portion. The first and second anchors may comprise respective upper and lower portions of a sleeve with the upper and lower portions being adapted for securing around respective ones of the leg and the foot.

23 Claims, 8 Drawing Sheets

(56) References Cited

U.S. PATENT DOCUMENTS

2010/0256544 A1 10/2010 Colon
2014/0012173 A1 1/2014 Newman

OTHER PUBLICATIONS

OPTP, "Stretch-EZ Product Description," http://www.optp.com/Stretch-EZ?kw=plantar#.VnBY7korLct, 2015, 1 page.
OPTP, "Plantar FXT Product Description," http://www.optp.com/Plantar-FXT#.VnBY5korLct, 2015, 1 page.

* cited by examiner

APPARATUS AND METHODS FOR TREATMENT OF PLANTAR FASCIITIS

FIELD

The field relates generally to treatment of impairments of the foot, and more particularly to the treatment of plantar fasciitis.

BACKGROUND

The plantar fascia is a thick band of connective tissue located in the sole of the foot. The plantar fascia connects the heel bone or calcaneus to the base of the toes or metatarsophalangeal joints, creating the soft tissue support of the arch of the foot. Plantar fasciitis is a condition characterized by inflammation, fibrosis or structural deterioration of the plantar fascia of the foot. Some contributing factors to this condition include flat feet, high arches, rigid feet, poor shoe support, increased age, sudden weight increase, sudden increase in activity or after return from a period of inactivity and even family history. Generally, patients suffering from plantar fasciitis experience a dull intermittent pain in the heel which may develop into a sharp persistent pain. The pain is usually in the front and bottom of the heel, but it can be over any portion of the bottom of the foot where the plantar fascia is located. Conventional treatments for plantar fasciitis include oral anti-inflammatories, ice packs, bed rest, stretching exercises, steroid injections, night splints and corrective surgery.

SUMMARY

Illustrative embodiments of the present invention provide apparatus and methods for the treatment of plantar fasciitis.

In one embodiment, an apparatus for treatment of plantar fasciitis comprises a first anchor adapted for securing around a leg of a patient or other human, a second anchor adapted for securing around a foot of the leg, first and second toe straps each adapted for attachment between the first and second anchors so as to provide respective first and second dorsiflexion forces to respective first and second subsets of toes of the foot, and a fascia compression strap comprising first and second ends and an intermediate portion between the first and second ends, the first and second ends each adapted for attachment to the first anchor so as to provide static pressure to an underside of the foot via the intermediate portion.

The first and second anchors may comprise, for example, respective upper and lower portions of a sleeve with the upper and lower portions being adapted for securing around respective ones of the leg and the foot. The first and second anchors may alternatively comprise respective entirely separate anchors.

The first and second toe straps in some embodiments comprise respective first and second bifurcated portions of one end of a bifurcated toe strap attached between the first and second anchors. The first and second toe straps may alternatively comprise respective entirely separate toe straps.

In another embodiment, an apparatus for treatment of plantar fasciitis comprises a first anchor adapted for securing around a leg of a patient or other human, a second anchor adapted for securing around a foot of the leg, and a plurality of straps including first and second toe straps and a fascia compression strap. The first toe strap comprises a first end and a second end, with the first and second ends adapted for attachment to respective ones of the first and second anchors so as to provide a first dorsiflexion force to a first subset of toes of the foot. The second toe strap comprises a first end and a second end, with the first and second ends adapted for attachment to respective ones of the first and second anchors so as to provide a second dorsiflexion force to a second subset of the toes of the foot. The fascia compression strap comprises first and second ends and an intermediate portion between the first and second ends, with the first and second ends each adapted for attachment to the first anchor so as to provide static pressure to an underside of the foot via the intermediate portion.

In yet another embodiment, a method for treatment of plantar fasciitis comprises securing a first anchor around a leg of a patient or other human, securing a second anchor around a foot of the leg, attaching first and second toe straps between the first and second anchors, so as to provide respective first and second dorsiflexion forces to respective first and second subsets of toes of the foot, and attaching first and second ends of a fascia compression strap to the first anchor so as to provide static pressure to an underside of the foot via an intermediate portion of the fascia compression strap.

In a further embodiment, a method for treatment of plantar fasciitis comprises applying a first dorsiflexion force to a first subset of toes of a human foot, applying a second dorsiflexion force to a second subset of the toes of the foot, and applying static pressure to an underside of the foot while the first and second dorsiflexion forces are applied to the respective first and second subsets of toes of the foot.

Advantageously, illustrative embodiments of the invention provide particularly efficient and effective arrangements for application of multiple distinct dorsiflexion forces to different subsets of toes of the foot in combination with application of static pressure to an area of the plantar fascia.

These and other features and advantages of the invention will become apparent from the following detailed description of illustrative embodiments thereof, which is to be read in connection with the accompanying drawings.

BRIEF DESCRIPTION OF THE DRAWINGS

FIGS. 1A, 2A, 3A, 4A and 5A and corresponding FIGS. 1B, 2B, 3B, 4B and 5B are also collectively referred to herein as respective FIGS. 1, 2, 3, 4 and 5.

FIGS. 6A, 7A and 8A and corresponding FIGS. 6B, 7B and 8B are also collectively referred to herein as respective FIGS. 6, 7 and 8.

DETAILED DESCRIPTION

As used herein, the term "first ray" refers to the foot segment consisting of the first metatarsal and the first cuneiform bones.

As used herein, the term "forefoot" refers to the segment of the foot consisting of the metatarsus and the phalanges.

As used herein, the term "dorsiflexion" refers to the flexion or bending of the foot such that the top of the foot moves toward the body, for example, such that the toes are brought closer to the shin.

As used herein, the term "anchor" refers to a strap, a cuff, a band, a strip, a sleeve, a half-sock, or any other arrangement of one or more materials that can be wrapped or fitted around a portion of the leg or foot.

As used herein, the term "great toe" refers to the first toe of the foot going from the medial side of the leg to the lateral side of the leg.

As used herein, the term "second toe to fifth toe" refers to the second, third, fourth and fifth toes of the foot going from the medial side of the leg to the lateral side of the leg.

As used herein, the term "intermediate portion" refers to the portion of a strap or anchor between a first end and a second end.

FIGS. 1 through 5 depict sequential application of an exemplary plantar fasciitis treatment apparatus 100 to a leg and foot of an individual according to an embodiment of the invention. The apparatus 100 is shown in its entirety only in FIGS. 5A and 5B. The other figures show sequential deployment of portions of the apparatus 100. More particularly, FIGS. 1 through 5 illustrate respective first, second, third, fourth and fifth steps in a method of treatment of plantar fasciitis using the apparatus 100. References herein to FIG. 1 should be understood to refer to both FIGS. 1A and 1B, and similarly for the remaining FIGS. 2 through 5 each of which also comprises A and B portions.

Figure 5A:
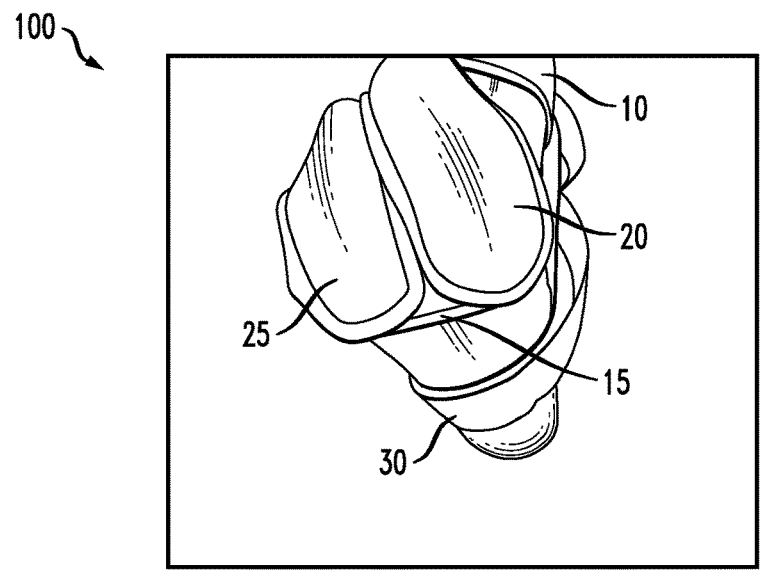
Figure 5B:
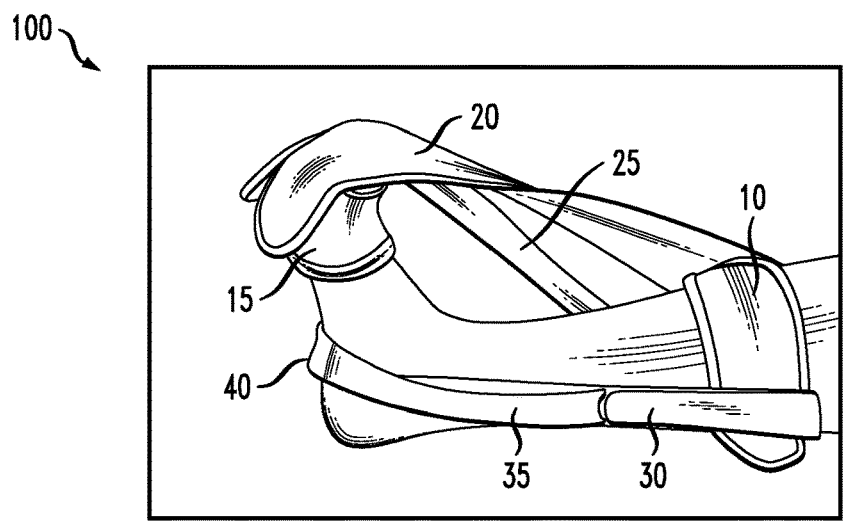

As indicated above, FIGS. 5A and 5B show respective front and side views of the apparatus 100 as deployed in an illustrative embodiment. The apparatus 100 as deployed illustratively comprises a first anchor 10 secured around the leg, a second anchor 15 secured around the foot, a first toe strap 20 attached to the first anchor 10 at one end and attached to the second anchor 15 on the other end, a second toe strap 25 attached to the first anchor 10 at one end and attached to the second anchor 15 on the other end, and a fascia compression strap 30 positioned under the arch of the foot with the two ends of the fascia compression 30 strap attached to the first anchor 10, according to an embodiment of the invention.

The manner in which the apparatus 100 is deployed in this embodiment will now be described in more detail with sequential reference to FIGS. 1 through 5.

Figure 1A:
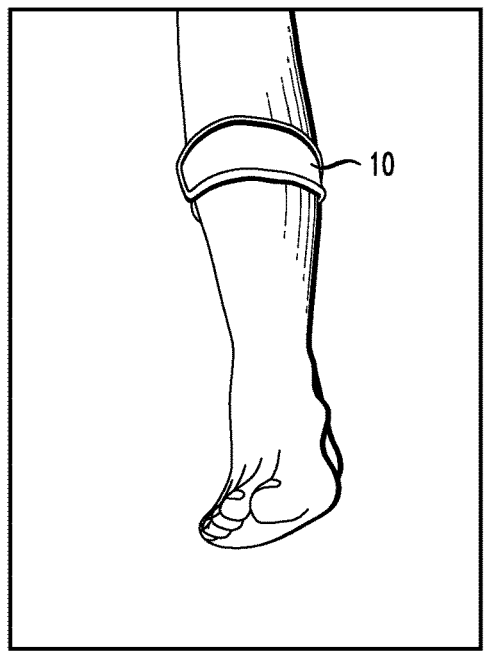
FIGS. 1A, 2A, 3A, 4A and 5A show respective front views illustrating sequential deployment of a plantar fasciitis treatment apparatus on a leg and foot of a patient, according to an embodiment of the invention.
Figure 1B:
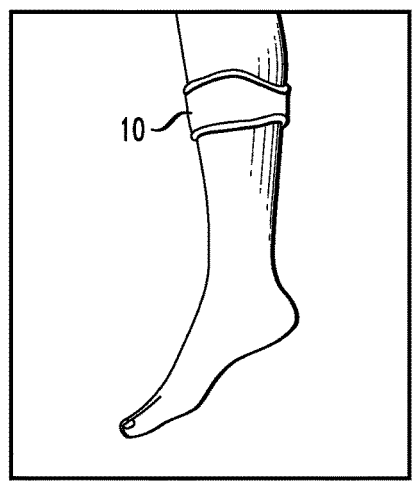
FIGS. 1B, 2B, 3B, 4B and 5B show respective side views corresponding to the front views of respective FIGS. 1A, 2A, 3A, 4A and 5A.

Referring to FIGS. 1A and 1B, a first anchor 10 is applied to a leg of the individual in the first step of applying the apparatus 100. In an illustrative application of first anchor 10 as shown in FIGS. 1A and 1B, the first anchor is fitted and secured around a mid-section of the calf. However, the first anchor can be applied to any portion of the leg below the knee or above the knee. Preferably, the first anchor is applied around the calf of the leg between the ankle and the knee. In an illustrative embodiment, the first anchor comprises a uniform strip adapted to receive one or more toe straps. In another illustrative embodiment, the first anchor may include one or more slits or openings suitable for guiding the various toe straps, through which the various toe straps may be pulled. Such slits or openings are examples of what are more generally referred to herein as "slotted guides."

The first anchor 10 shown in FIG. 1 is secured around the calf using hook-and-loop fasteners, such as the hook-and-loop fasteners commercially available from Velcro®. Other fastening means that allow for adjustment to accommodate the circumference of the calf may be used, including but not limited to D-rings, snaps, tape, buttons and any other fastening mechanisms known in the art.

Figure 2A:
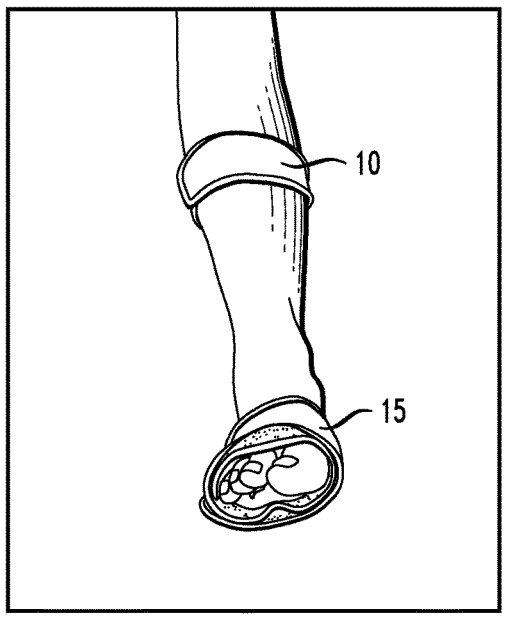
Figure 2B:
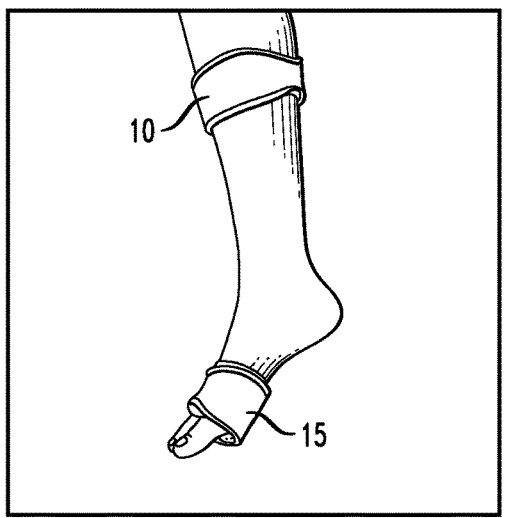

FIGS. 2A and 2B show the second step of applying apparatus 100 to the leg of the individual, in which a second anchor 15 is fitted and secured around the foot of the leg. The second anchor 15 is preferably positioned around the forefoot region of the foot, but may be positioned anywhere along the foot. The second anchor 15 can be secured around the foot using any fastening means, such as those described above with respect to the first anchor 10. Alternatively, the second anchor 15 may be a sleeve or half-sock, which covers the forefoot and/or the mid-foot, leaving the heel bare.

Figure 3A:
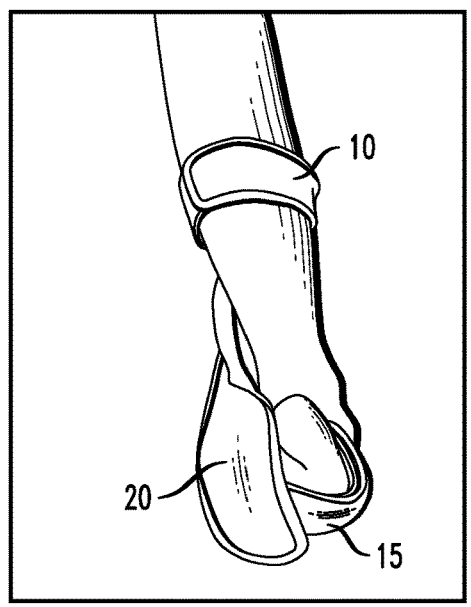
Figure 3B:
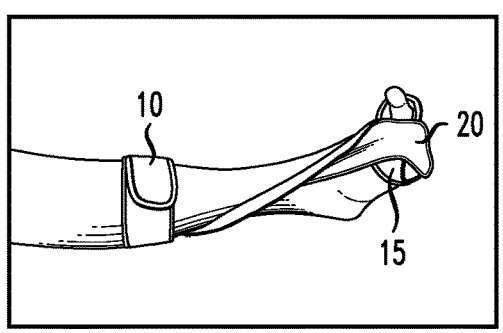

FIGS. 3A and 3B show the third step in applying apparatus 100 to the leg of the individual, in which a first toe strap 20 is attached to the first anchor 10 at one end and attached to the second anchor 15 at a second end. The first toe strap 20 may be attached to any portion of the first anchor 10 and to any portion of the second anchor 15 so as to provide a dorsiflexion force to the foot. In the illustrative application of apparatus 100 shown, the first toe strap 20 is attached to the second anchor 15 on the plantar side of the foot and attached to first anchor 10 on the posterior side of the calf. The first toe strap 20 is attached to the first and second anchors in a tensioned manner to provide for dorsiflexion of the foot.

The two ends of the first toe strap 20 shown contain a hook-and-loop fastening mechanism for coupling to the first and a second anchors. Alternatively, other fastening mechanisms, such as those described above with respect to the first anchor, may be used. Still further, the first toe strap 20 may be permanently affixed to the second anchor 15, e.g., sewn onto the second anchor 15. The first toe strap 20 may span one or more of the second to fifth toes of the foot, as such the width of the first toe strap 20 may vary accordingly.

Figure 4A:
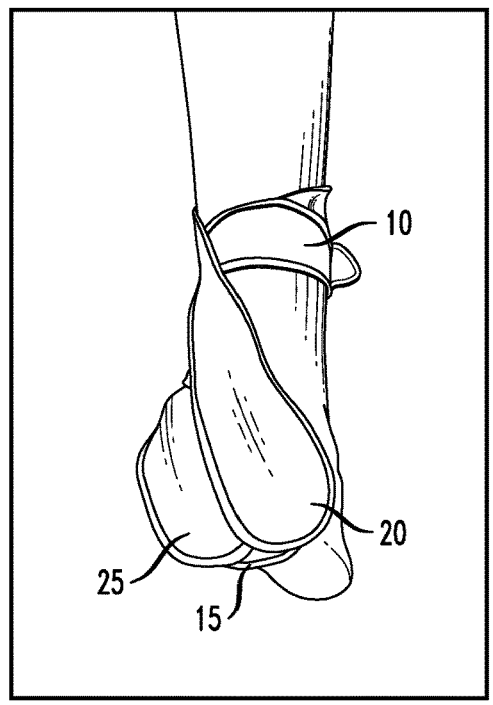
Figure 4B:
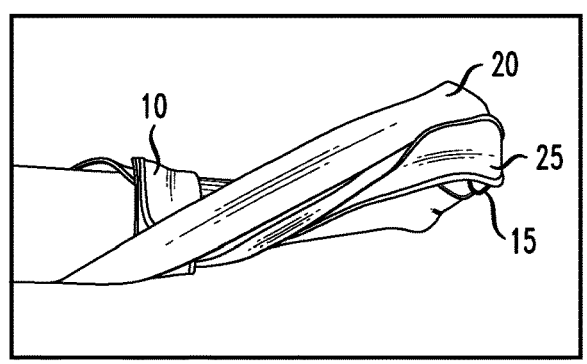

FIGS. 4A and 4B show the fourth step in applying the apparatus 100 to the leg of the individual. A second toe strap 25 is applied to the leg in a manner similar to the application of the first toe strap 20 described above.

In the illustrative application of the portions of apparatus 100 shown, the second toe strap 25 is attached to the second anchor 15 on the plantar side of the foot and attached to the first anchor 10 on the posterior side of the calf. The first toe strap 20 is attached to the first and second anchors in a tensioned manner to provide for dorsiflexion force as well as first ray dorsiflexion force to the foot. The second toe strap 25 may span the great toe of the foot and optionally span one or more of the second to fifth toes of the foot. The second toe strap 25 is preferably positioned adjacent to the first toe strap 20 at the points of attachment to the first anchor 10 and/or second anchor 15, and may optionally overlap with the first toe strap 20. The width of the second toe strap 25 may also vary according to its intended application.

The two ends of the second toe strap 25 as shown contain a hook-and-loop fastening mechanism for coupling to the first and a second anchors. Alternatively, other fastening mechanisms, such as those described above with respect to the first anchor 10, may be used. Still further, the second toe strap 25 may be permanently affixed to the second anchor 15, e.g., sewn onto the second anchor 15 adjacent to the first toe strap 20.

Application of the first toe strap 20 and the second toe strap 25 to the first anchor 10 maintains the toes in a dorsiflexed position, which can be beneficial in the treatment of plantar fasciitis and similar conditions that benefit from dorsiflexion of the foot and/or toes. The amount of dorsiflexion can be adjusted by adjusting the tension provided by the first toe strap 20 and the second toe strap 25 and/or adjusting the position of the first anchor 10 along the calf. Furthermore, the first toe strap 20 and second toe strap 25 may also be attached to the first anchor 10 in a manner to create inversion of the forefoot which causes more tension to the plantar fascia. For example, the first toe strap 20 and second toe strap 25 can be attached to the first anchor 10 on the lateral or posterior side of the calf. Preferably, the user's toes are flexed up during application of the first and second toe straps to the first anchor, thereby causing a medial to lateral rotation of the foot and/or toes while maintaining the toes in a dorsiflexed position.

FIGS. 5A and 5B show the last step in applying the apparatus 100 to the leg of the individual. A fascia compression strap 30 is applied to the leg by positioning the intermediate portion of the fascia compression strap 30 under the arch of the foot. The two ends of the fascia compression strap 30 may be attached to the first anchor 10 on any portion of the first anchor 10. In the illustrative application of apparatus 100 shown, the two ends of the fascia compression strap 30 attaches to the first anchor 10 at the lateral and medial sides of the leg.

The fascia compression strap 30 may also contain an adjustable segment 35 to modify the length of the fascia compression strap 30 so as to accommodate different positioning of the first anchor 10 along the leg. The adjustable segment can be adjusted using any known strap adjusting mechanism, including but not limited to slide adjusters, buckles, D-rings, and hook-and-loop fasteners.

An object 40 may be placed or inserted between the fascia compression strap 30 and the plantar surface of the foot to provide static pressure to an area of the plantar fascia. For example, a common area of pain associated with plantar fasciitis is the region under the arch near the heel of the foot. The object 40 can be placed at that specific area to provide directed static pressure to the plantar fascia. The object 40 may be a ball, a roller, a pad, a cushion or combinations thereof. Preferably, the object is of a suitable size spanning the width of at least a portion of the plantar fascia, e.g., an object of a cylindrical shape having a length of about 1" to 2" so as to span at least a portion of the width of the plantar fascia.

Numerous alternative arrangements are possible. For example, the object 40 may be made integral with the fascia compression strap 30, such that it is "built in" to the strap in an appropriate location corresponding generally to the underside of the foot.

As another example, the object 40 can comprise an ice cube pouch configured to provide focal ice compression in cooperation with the fascia compression strap 30. Such a pouch can also be formed at least in part integrally with the fascia compression strap 30, or as an entirely separate element.

Still further, the second anchor may be provided as a single piece of material (e.g., one piece of fabric spanning the length and width of the plantar fascia, a sock, a half-sock, etc.) suitable for attachment of the first toe strap and the second toe strap. The second anchor may be also be temporarily affixed or permanently affixed to the first anchor at a distal end of the first anchor. For example, the second anchor may be sewn onto a distal end of the first anchor. Alternatively, the first and second anchor may include hook-and-loop fasteners for temporary attachment thereto.

The two ends of the fascia compression strap 30 shown in the figures illustratively comprise a hook-and-loop fastening mechanism for coupling to the first anchor 10. Alternatively, other fastening mechanisms, such as those described above with respect to the first anchor, may be used. Furthermore, the fascia compression strap may include one or more additional pull straps to create additional tension to the plantar fascia. Still further, more than one fascia compression strap and object may be applied to the plantar fascia to create additional tension to the plantar fascia.

The duration of application may vary as desired or needed, for example, depending on physician instructions and/or severity of the condition being treated. As an example, a user may apply this apparatus to the site of discomfort for 10 minutes to 20 minutes every day for a week. It is to be noted that while an illustrative embodiment described herein contains two toe straps, a patient or his physician may choose to use only one of the toe straps during the course of treatment.

The straps and anchors of apparatus 100 may be constructed from any suitable material, including but not limited to nylon, leather, woven fibers, and elasticized woven fabric tapes. The straps and anchors may be constructed from the same material or from different materials. Moreover, various arrangements of built-in straps are possible.

In addition, the first and second toe straps can illustratively comprise respective first and second portions of a bifurcated toe strap that has separate first ends for attachment to the first anchor but common second ends that are attached as a substantially unitary element to the second anchor. Such a substantially unitary element may be part of a sleeve, half-sock or other similar anchoring arrangement that can be secured to the foot.

The particular embodiment illustrated in FIGS. 1 through 5 is one possible example of an embodiment that utilizes entirely separate first and second anchors and entirely separate first and second toe straps as part of the apparatus. It was noted above that numerous integrated arrangements of anchors and straps may be used.

By way of further example, in other embodiments, the first and second anchors may comprise respective upper and lower integrated portions of a sleeve with the upper and lower portions being adapted for securing around respective ones of the leg and the foot. Additionally, the first and second toe straps in some embodiments may comprise respective first and second bifurcated portions of one end of a bifurcated toe strap attached between the first and second anchors.

A more particular example of an arrangement of this type is the illustrative embodiment shown in various views in FIGS. 6 through 8, of which FIGS. 6 and 7 show different views of an apparatus 600 for the treatment of plantar fasciitis prior to deployment on a patient, and FIG. 8 shows two different views of the apparatus 600 as deployed on a patient.

Figure 6A:
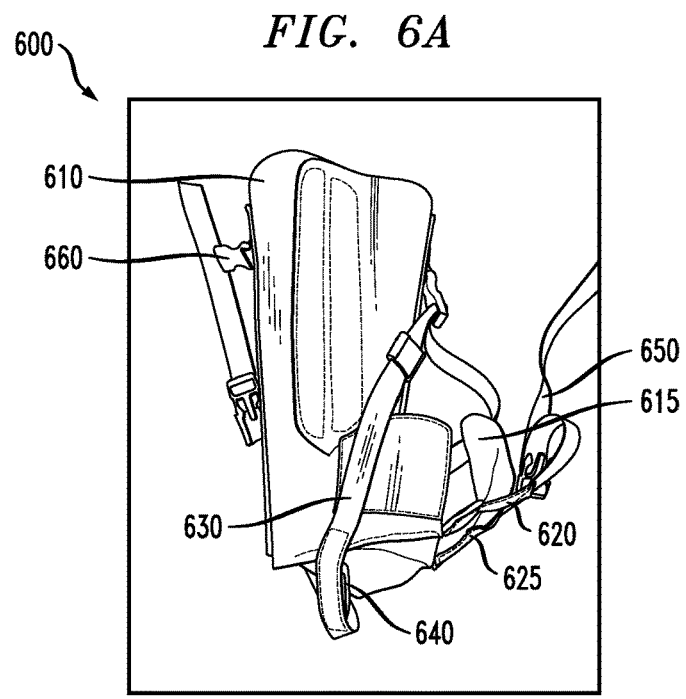
FIGS. 6A, 6B, 7A, 7B, 8A and 8B show various views of another illustrative embodiment of an apparatus for treating plantar fasciitis, in which upper and lower portions of a sleeve are used to form at least a portion of respective first and second anchors.
Figure 6B:
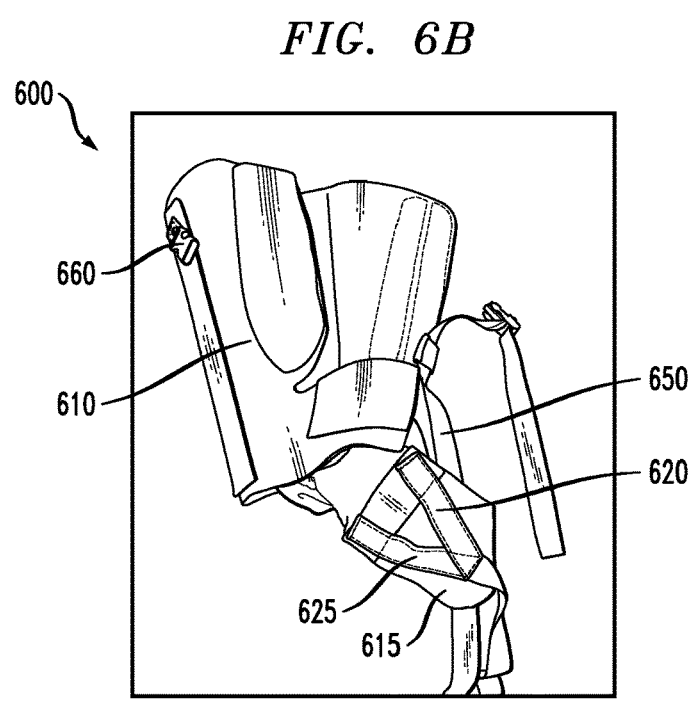

As shown in FIGS. 6A and 6B, the apparatus 600 comprises a sleeve 610 with upper and lower portions. An upper portion of the sleeve 610 provides a first anchor suitable for wrapping around a lower leg of a patient. The lower portion of the sleeve 610 in combination with a fabric piece 615 provides a second anchor suitable for wrapping around a foot of the patient. The first and second anchors are secured about the respective lower leg and foot of the patient using hook-and-loop fasteners that are affixed to the sleeve 610, although numerous other fastening mechanisms may be used in other embodiments.

The apparatus 600 further comprises first and second toe straps 620 and 625 that comprise respective first and second bifurcated portions of one end of a bifurcated toe strap 650 attachable between the first and second anchors. More particularly, a first end of the bifurcated toe strap is attachable to the first anchor at an upper portion of the sleeve 610, using a mating clip arrangement as illustrated. The second end of the bifurcated toe strap 650 includes portions comprising respective ones of the first and second toe straps 620 and 625 that are affixed to the fabric piece 615, and more particularly are sewn into the fabric piece 615 in this embodiment.

The bifurcated toe strap 650 comprising first and second toe straps 620 and 625 at one end thereof is considered one possible example of an arrangement comprising first and second toe straps each adapted for attachment between the first and second anchors associated with sleeve 610, so as to provide respective first and second dorsiflexion forces to respective first and second subsets of toes of the foot.

An example of a mating clip attached to the first anchor at an upper portion of the sleeve 610 is the mating clip 660. Similar mating clip arrangements are utilized in this embodiment for the first end of the bifurcated toe strap 650, and for both ends of an adjustable fascia compression strap 630. Male mating clips are attached to the respective ends of the straps and corresponding female mating clips are arranged on the first anchor at an outer surface of the sleeve 610 so as to facilitate attachment of the strap ends to the first anchor.

As can be seen in FIG. 6B, the mating clip 660 is arranged on the first anchor in this embodiment using hook-and-loop fasteners. More particularly, the outer surface of the sleeve 610 in this embodiment includes multiple longitudinally-arranged hook-and-loop fastener strips to enable attachment of corresponding mating clips at different locations along the outer surface of the sleeve 610. These mating clips are used for attachment of first and second ends of the fascia compression strap 630.

Figure 7A:
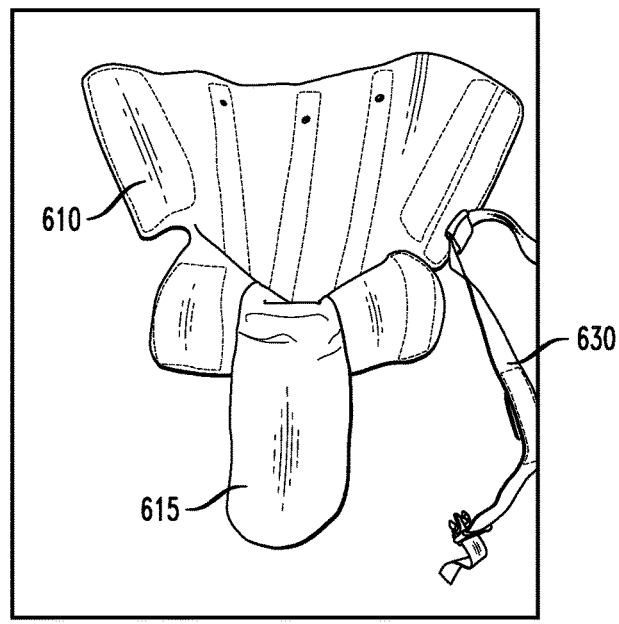
Figure 7B:
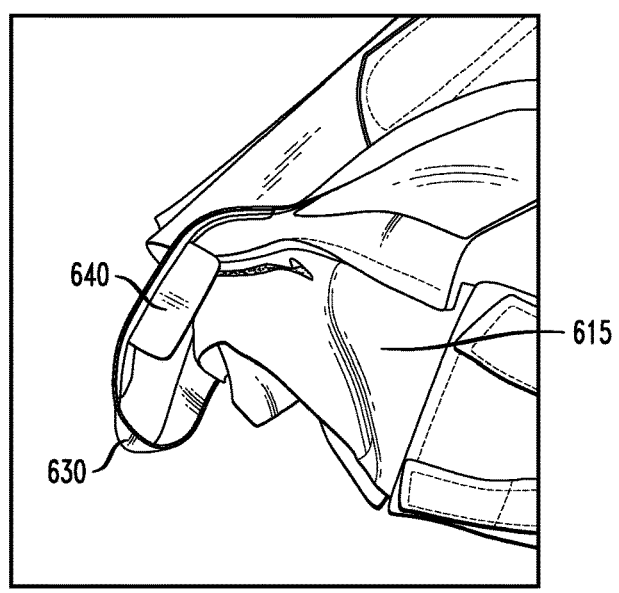

With reference to FIG. 7A, the sleeve 610 is shown in an opened arrangement, so as to reveal the inner surface of the sleeve. As mentioned above, an upper portion of the sleeve 610 provides the first anchor in this embodiment, and a lower portion of the sleeve 610 in combination with a fabric piece 615 secured to the lower portion of the sleeve 610 provides the second anchor in this embodiment. The fabric piece 615 substantially spans the length and width of the plantar fascia during use of the apparatus 600. Also visible in FIG. 7A is a portion of the fascia compression strap 630 and an associated slotted guide affixed to the sleeve 610. The fascia compression strap 630 as shown in FIG. 7B includes an attached object 640 for use in applying static pressure to an underside of the foot when the apparatus 600 is deployed on a patient. The object 640 is illustratively attached to the fascia compression strap 630 using hook-and-loop fasteners.

The fascia compression strap 630 is considered one possible example of a fascia compression strap having first and second ends and an intermediate portion between the first and second ends, with the first and second ends each being adapted for attachment to the first anchor, illustratively implemented by part of sleeve 610, so as to provide static pressure to an underside of the foot via the intermediate portion.

Figure 8A:
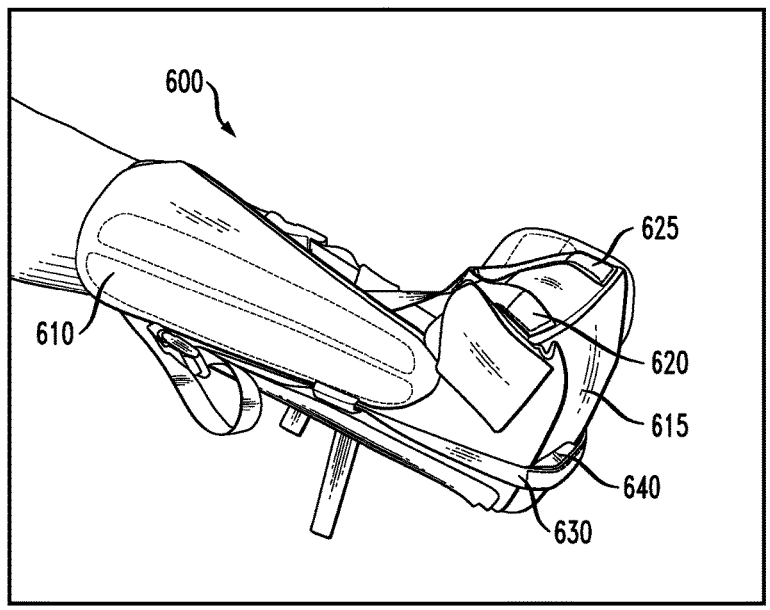
Figure 8B:
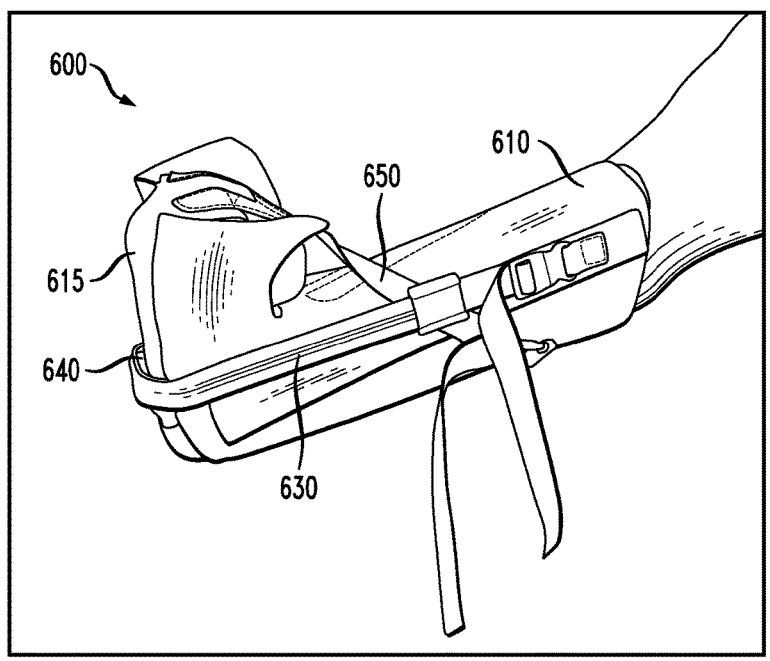

FIGS. 8A and 8B show different views of the apparatus 600 when deployed on a patient. It can be seen that both ends of the fascia compression strap 630 pass through respective slotted guides and include respective adjustment mechanisms for varying the amount of compressive force applied to the plantar fascia area of the foot. The bifurcated toe strap 650 can be similarly secured at its first end to the first anchor at an upper portion of the sleeve 610, and may also be made adjustable in length.

As in previous embodiments, any of a wide variety of materials, shapes and configurations may be utilized for the object 640. For example, various cylindrical, round, curvilinear or rectangular shapes may be used. The object 640 may therefore comprise a cylindrical element, a ball, a roller or other type of object suitable for use in conjunction with the fascia compression strap 630 in applying static pressure to an area of the plantar fascia.

The particular arrangements of sleeve, anchors and straps illustrated in FIGS. 6 through 8 are exemplary only. For example, numerous other sleeve configurations may be used to provide first and second anchors for securing around the respective leg and foot of a patient during treatment. Terms such as "anchors" and "secure around" as used herein are therefore intended to be broadly construed. For example, the term "secure around" when used in conjunction with a particular anchoring arrangement should not be viewed as requiring that the arrangement fully surround or otherwise encompass the leg or foot.

It is important to note that one or more steps described herein may be performed in a different order. For example, with reference to the embodiment of FIGS. 1 through 5, application of the second anchor 15 around the foot may be performed before application of the first anchor 10 around the calf of the leg. As another example, the second toe strap 25 may be attached before the first toe strap 15. Numerous other variations can be made to the exemplary steps described in conjunction with illustrative embodiments herein.

It is to be understood that the invention is not limited to the illustrative embodiments described in detail herein with reference to the figures. As such, modifications and variations will be apparent to those skilled in the art. For example, the apparatus 100 or 600 may include different numbers, types and arrangements of anchors, toe straps and fascia compression straps from the illustrative embodiments shown in the figures. Various arrangements of integrated or separate components can be used. As another example, the toe straps may each be a separate strip or may be strips cut from one piece of material such that the straps are still attached on one end. Numerous other variations or modifications in the arrangement of the components of the apparatus 100 or 600 may be used.

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

What is claimed is:

1. An apparatus comprising:
   a first anchor configured for securing around a human leg;
   a second anchor configured for securing around a foot of the leg;
   first and second toe straps each configured for attachment between the first and second anchors, the first and second toe straps each configured to be placed under tension so as to provide respective first and second dorsiflexion forces to respective first and second subsets of toes of the foot; and
   a fascia compression strap comprising first and second ends and an intermediate portion between the first and second ends, the intermediate portion of the fascia compression strap configured for positioning about an underside of the foot with the first and second ends extending in a direction toward the first anchor, the first and second ends of the fascia compression strap each directly attachable to the first anchor under tension so as to provide static pressure to the underside of the foot via the intermediate portion.

2. The apparatus of claim 1 wherein:
the first toe strap comprises a first end and a second end, the first and second ends configured for attachment to respective ones of the first and second anchors so as to provide the first dorsiflexion force to the first subset of toes of the foot; and
the second toe strap comprises a first end and a second end, the first and second ends configured for attachment to respective ones of the first and second anchors so as to provide the second dorsiflexion force to the second subset of toes of the foot.

3. The apparatus of claim 2 wherein the first toe strap and the second toe strap at least partially overlap with one another at their respective first ends upon attachment of the first ends to the first anchor.

4. The apparatus of claim 2 wherein the first toe strap and the second toe strap at least partially overlap with one another at their respective second ends upon attachment of the second ends to the second anchor.

5. The apparatus of claim 2 wherein the first and second ends of the second toe strap are configured for attachment to respective ones of the first and second anchors so as to provide the second dorsiflexion force and a ray force to the second subset of the toes of the foot.

6. The apparatus of claim 2 wherein the first toe strap and the second toe strap are permanently attached to the second anchor at their respective second ends.

7. The apparatus of claim 1 wherein the first and second anchors comprise respective upper and lower portions of a sleeve with the upper and lower portions being configured for securing around respective ones of the leg and the foot.

8. The apparatus of claim 1 wherein the first toe strap is configured to provide the first dorsiflexion force to a first subset of toes and the second toe strap is configured to provide the second dorsiflexion force to a second subset of toes, the first subset of toes being at least one of a second toe to a fifth toe of the foot and the second subset of toes being at least a great toe of the foot.

9. The apparatus of claim 1 wherein the first and second toe straps comprise respective first and second bifurcated portions of one end of a bifurcated toe strap and being configured for attachment between the first and second anchors.

10. The apparatus of claim 1 further comprising at least one object configured to be held against the underside of the foot by the intermediate portion of the fascia compression strap.

11. The apparatus of claim 1 wherein the fascia compression strap comprises at least one adjustable segment for permitting lengthwise adjustment.

12. The apparatus of claim 1 wherein the second anchor comprises at least a portion of one or more of a sleeve, a half-sock, and a single piece of material.

13. The apparatus of claim 1 wherein the first anchor comprises at least one of a slotted guide and a fastener configured to receive an end of at least one of the first and second toe straps.

14. The apparatus of claim 1 wherein the first and second toe straps and the first anchor include respective hook-and-loop fasteners to secure each of the first and second toe straps to the first anchor, and wherein the first and second ends of the fascia compression strap and the first anchor include hook-and-loop fasteners to secure the first and second ends of the fascia compression strap to the first anchor.

15. A method comprising:
securing a first anchor around a human leg;
securing a second anchor around a foot of the leg;
attaching first and second toe straps between the first and second anchors, so as to provide respective first and second dorsiflexion forces to respective first and second subsets of toes of the foot;
positioning a fascia compression strap around an underside or arch of the foot; and
directly attaching first and second ends of the fascia compression strap to the first anchor so as to provide static pressure to the underside or arch of the foot via an intermediate portion of the fascia compression strap.

16. The method of claim 15 wherein the first and second anchors comprise respective upper and lower portions of a sleeve and wherein securing the first anchor includes positioning the upper portion of the sleeve around the leg and wherein securing the second anchor includes positioning the lower portion of the sleeve about the foot.

17. The method of claim 15 wherein the first subset of toes comprises at least one of a second toe to a fifth toe of the foot and the second subset of toes comprises at least a great toe of the foot.

18. The method of claim 15 wherein attaching the first and second toe straps between the first and second anchors further comprises:
attaching first and second ends of the first toe strap to respective ones of the first and second anchors so as to provide the first dorsiflexion force to the first subset of toes of the foot; and
attaching first and second ends of the second toe strap to respective ones of the first and second anchors so as to provide the second dorsiflexion force to the second subset of the toes of the foot.

19. The method of claim 15 further comprising holding at least one object against the underside or arch of the foot by the intermediate portion of the fascia compression strap.

20. The method of claim 15 wherein the first and second toe straps comprise respective first and second bifurcated portions of one end of a bifurcated toe strap attached between the first and second anchors.

21. A method comprising:
applying a first dorsiflexion force to a first subset of toes of a human foot by extending a first strap between a first subset of toes and a leg and maintaining the first strap under tension;
applying a second dorsiflexion force to a second subset of the toes of the foot by extending a second strap between the second subset of toes and the leg and maintaining the second strap under tension; and
applying static pressure to an underside of the foot by wrapping a fascia compression strap around the underside or arch of the foot and extending opposed end sections of the fascia compression strap to the leg of the subject and maintaining the opposed end sections under tension while the first and second dorsiflexion forces are applied to the respective first and second subsets of toes of the foot.

22. The method of claim 21 wherein the first and second dorsiflexion forces are applied via respective first and second bifurcated portions of one end of a bifurcated toe strap attached between first and second anchors.

23. The method of claim 21 including:
positioning a first anchor about the leg and positioning a second anchor about the foot; and
wherein applying the first dorsiflexion force includes securing the first strap to the first and second anchors;

wherein applying the second dorsiflexion force includes securing the second strap to the first and second anchors; and wherein applying static pressure to the underside or arch of the foot includes securing the opposed end sections of the fascia compression strap to the first anchor.

* * * * *